(12) United States Patent
McDermott (10) Patent No.: US 7,357,772 B2
(45) Date of Patent: Apr. 15, 2008

(54) PATIENT-SUPPORT APPARATUS HAVING LINE MANAGEMENT SYSTEM

(75) Inventor: Ian McDermott, Lincoln University, PA (US)

(73) Assignee: Draeger Medical Systems, Inc., Telford, PA (US)

( * ) Notice: Subject to any disclaimer, the term of this patent is extended or adjusted under 35 U.S.C. 154(b) by 497 days.

(21) Appl. No.: 10/490,796

(22) PCT Filed: Oct. 3, 2002

(86) PCT No.: PCT/US02/31408

§ 371 (c)(1),
(2), (4) Date: Mar. 25, 2004

(87) PCT Pub. No.: WO03/030797

PCT Pub. Date: Apr. 17, 2003

(65) Prior Publication Data

US 2004/0186341 A1 Sep. 23, 2004

Related U.S. Application Data

(60) Provisional application No. 60/327,496, filed on Oct. 5, 2001, provisional application No. 60/373,417, filed on Apr. 17, 2002.

(51) Int. Cl.
*A61G 11/00* (2006.01)
(52) U.S. Cl. ....................................................... 600/22
(58) Field of Classification Search ............ 600/21–22; 604/77, 79, 80, 174, 177; 128/205.26, 845–847, 128/872; 135/121; 52/27, 36.4; 5/93.1, 5/414, 416, 424, 600, 603, 415; 312/1, 223.1, 312/223.6; 211/26; 174/1, 480–481, 500–506
See application file for complete search history.

(56) References Cited

U.S. PATENT DOCUMENTS

| 2,663,608 | A |   | 12/1953 | Schauer |
|-----------|---|---|---------|---------|
| 3,470,866 | A |   | 10/1969 | Gittelson |
| 3,858,570 | A | * | 1/1975 | Beld et al. ..................... 600/22 |
| 5,224,674 | A | * | 7/1993 | Simons ..................... 248/68.1 |
| 5,308,310 | A | * | 5/1994 | Roff et al. ..................... 600/21 |
| 5,387,177 | A | * | 2/1995 | Dunn ......................... 600/22 |

(Continued)

FOREIGN PATENT DOCUMENTS

DE 73 34 435.1 1/1974

(Continued)

*Primary Examiner*—Samuel G Gilbert
(74) *Attorney, Agent, or Firm*—Caesar, Rivise, Bernstein, Cohen & Pokotilow, Ltd.

(57) ABSTRACT

An infant support device (10) is provided and includes a support platform (26), an infant enclosure (34) coupled to the support platform (26) and defining an infant compartment for receiving an infant (78), and a line-management apparatus configured to separate and arrange medical lines (54) routed between the outside of the infant compartment and the inside of the infant compartment. One embodiment of the line-management apparatus includes a panel (46) extending upwardly relative to the support platform (26), a plurality of vertically spaced line supports (58) coupled to the panel (46) and configured to support the medical lines (54) resting thereon, and a plurality of line holders (60) coupled to the panel (46) and configured to inhibit movement of the medical lines (54) off of the line supports (58).

17 Claims, 5 Drawing Sheets

U.S. PATENT DOCUMENTS

| | | | |
|---|---|---|---|
| 6,049,924 A * | 4/2000 | Prows et al. ................... | 5/427 |
| 6,210,320 B1 | 4/2001 | Rogone et al. | |
| 6,310,294 B1 * | 10/2001 | Di Girolamo et al. ...... | 174/101 |
| 6,336,897 B1 * | 1/2002 | Mackin ....................... | 600/22 |
| 6,367,476 B1 | 4/2002 | Conn | |
| 6,375,017 B1 | 4/2002 | Schattner et al. | |
| 2001/0035702 A1 | 11/2001 | Murphy et al. | |

FOREIGN PATENT DOCUMENTS

| | | |
|---|---|---|
| DE | 24 33 882 | 2/1976 |
| DE | 32 05 097 A1 | 10/1982 |
| DE | 39 15 882 A1 | 11/1990 |
| DE | 42 28 873 C1 | 10/1993 |
| DE | 297 09 848 U1 | 10/1997 |
| WO | WO 99/12511 A1 | 3/1999 |
| WO | WO 00/69387 A1 | 11/2000 |

* cited by examiner

PATIENT-SUPPORT APPARATUS HAVING LINE MANAGEMENT SYSTEM

CROSS-REFERENCE TO RELATED APPLICATIONS

This application is a U.S. national counterpart application of international application serial no. PCT/US02/31408 filed Oct. 3, 2002, which claims the benefit of U.S. provisional applications Ser. Nos. 60/327,496 and 60/373,417 filed Oct. 5, 2001, and Apr. 17, 2002, respectively.

BACKGROUND AND SUMMARY OF THE INVENTION

The present disclosure relates to a patient-support apparatus, and particularly to a patient-support apparatus having a line management system. More particularly, the present disclosure relates to a patient-support apparatus having a port integrated into an infant enclosure, or in the alternative, a patient-support apparatus having a port integrated into an infant supporting portion.

Thermal support devices, such as infant warmers and incubators, having an isolation chamber and various systems that maintain the isolation chamber at a controlled temperature and humidity to facilitate the development of a premature infant are known. Infant thermal support devices conventionally include a patient-support surface for supporting the infant in the isolation chamber and a set of side guard panels arranged around the patient-support surface. Many thermal support devices have a canopy over the patient-support surface. The canopy cooperates with the set of side guard panels to enclose the isolation chamber.

In such support devices, it is common to have a number of lines, both electronic and fluid, which communicate with the infant. These lines are conduits for electric signals, body fluids, oxygen, or any other substance that might be carried or transmitted either toward or away from the infant. At times, it may be desired to remove one line while leaving the remaining lines undisturbed, and it would therefore be advantageous to have the lines arranged and separated in an organized fashion.

The infant enclosure includes a side panel extending upwardly from the support platform and the door panel is aligned in side-by-side relation with the side panel when the door panel is in the first position. An end panel is also coupled to the support platform. A gap is defined between the door panel and the end panel when the door panel is in the first position, and each of the medical lines supported on the plates extends through the gap.

The infant enclosure further includes a canopy situated above the infant compartment. The canopy has a bottom edge, and the door panel has a top edge that confronts the bottom edge of the canopy when the door panel is in the first position.

The illustrative plurality of line holders comprises a plurality of flexible fingers that engage the medical lines. The plurality of flexible fingers is grouped into pairs, each pair being associated with a respective one of the plurality of line supports. The flexible fingers of each pair extend away from the panel and have a distal end spaced apart from the panel. A slot is defined between the distal ends of each pair of flexible fingers, and the medical lines are inserted through the slots to be retained by the flexible fingers.

In another illustrative embodiment, an infant support device comprises a support platform having an interior region, an infant enclosure coupled to the support platform and defining an infant compartment for receiving an infant, a first line connector coupled to the support platform and situated outside the infant compartment, a second line connector coupled to the support platform and situated inside the infant compartment, and an internal connection line situated at least partly in the interior region. The internal connection line is coupled to the first line connector and to the second line connector.

According to one embodiment, a patient-support apparatus comprises a base, a patient support carried by the base, and a substantially planar guard panel configured to extend upwardly from the base on at least one side of the patient support. The guard panel includes a line port having a line holder and a line support.

The port has a wall defining a first plane substantially parallel to the guard panel, and the port has a second surface defining a second plane angled from the first plane. The port wall cooperates with the guard panel to define a vertically extending slot therebetween.

An access door substantially covers the defined slot. The access door is pivotably connected to the base. The access door contacts the line support when the access door is in a closed position. The line holder and line support are coupled to the port wall along a substantially horizontal line. The line support extends substantially orthogonally from the port wall and is configured to support a line thereon. The line holder is a clasp and is configured to retain a line therein. In one embodiment, the line holder has two fingers extending substantially orthogonally from the port wall. The line port is positioned on one end of the guard panel and can be either secured to the guard panel, or pivotably connected.

According to an aspect of this disclosure, the patient-support apparatus comprises a patient support, a substantially planar guard panel coupled to the patient support, and a line support coupled to the guard panel. The line support is adapted to separate and arrange lines passing through the planar side guard panel.

The disclosure provides for a patient-support apparatus that is configured to present electrical sensors to a patient. The apparatus comprises a base, a patient support, an electronic terminal mounted on the base and in electronic communication with the sensors, and a monitor configured for electronic communication with the terminal. The terminal includes a plurality of electrodes and is illustratively detachable. A second terminal can be mounted on the patient support, the second terminal being in electronic communication with the first terminal. Wires connect the first terminal to the second terminal, and the wires are housed within the base. Sensors connect to the second terminal. The first terminal illustratively includes a plurality of detachable modules.

A wire management device includes a plurality of sensors, each for sensing a condition of the patient, a plurality of wires in electrical communication with the sensors, and a wire port having a plurality of receivers adapted to receive the plurality of wires. In such an embodiment, the wire port is an electronic terminal and the receivers are electrodes. The wire port is coupled to the base of the patient-support apparatus.

The patient-support apparatus includes four guard panels configured to extend upwardly from the base and define a parallelogram, and the patient-support apparatus further includes a second wire port mounted within the perimeter of the defined parallelogram. A substantially planar guard panel is configured to extend upwardly from the base on at least one side of the patient support, and the wire port is coupled to the guard panel and the receivers are configured to hold the wires in place.

Additional features will become apparent to those skilled in the art upon consideration of the following detailed description of preferred embodiments exemplifying the best mode of carrying out the patient-support apparatus having a line management system as presently perceived.

BRIEF DESCRIPTION OF THE DRAWINGS

The detailed description particularly refers to the accompanying figures in which.

DETAILED DESCRIPTION OF THE DRAWINGS

Figure 1:
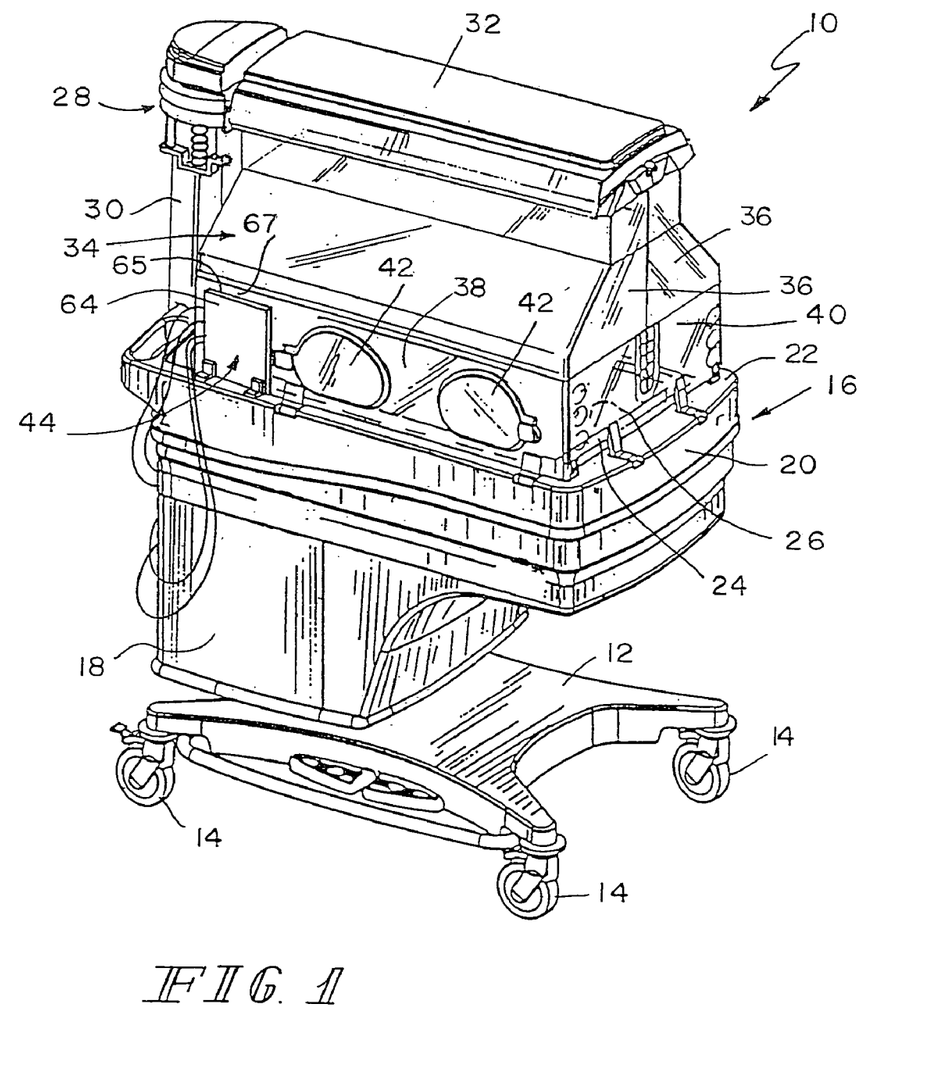
FIG. 1 is a perspective view of a patient-support apparatus according to the present disclosure showing a base, a patient support carried above the base, and an isolation chamber enclosed by an overlying canopy, a pair of transparent side guard panels, and a pair of transparent end panels, and further showing a line port having an access door.

A patient-support apparatus 10, such as an infant warming device or incubator, illustratively includes a base 12, a plurality of casters 14 extending downwardly from the base 12, and an infant supporting portion or patient support 16 supported above base 12 as shown in FIG. 1. Illustrative patient support 16 includes a pedestal 18 coupled to base 12 for vertical movement, a platform tub 20 supported by pedestal 18, a platform cover 22 coupled to platform tub 20, and a mattress 24 supported on platform tub 20. Mattress 24 has an upwardly facing patient-support surface 26.

Patient-support apparatus 10 also includes a canopy support arm 28 including a telescoping vertical arm 30 and a horizontal overhead arm 32. A canopy 34 is coupled to overhead arm 32 and is positioned to lie above platform tub 20. Canopy 34 includes a pair of canopy halves 36 coupled to overhead arm 32 for pivoting movement between a lowered position shown in FIG. 1 and a raised position (not shown).

A pair of transparent side guard panels 38 and a pair of transparent end guard panels 40 extend upwardly from platform tub 20 as shown in FIG. 1. Side guard panels 38 and end guard panels 40 cooperate with canopy halves 36 and overhead arm 32 to provide patient-support apparatus 10 with an isolation chamber. Side guard panels 38 are illustratively formed to include a pair of access ports 42, as shown in FIG. 1.

According to the present disclosure, patient-support apparatus 10 further includes a line management system as disclosed herein. In one embodiment, the line management system includes a line port 44, as shown in FIG. 1 and in more detail in FIGS. 2 and 3.

Figure 2:
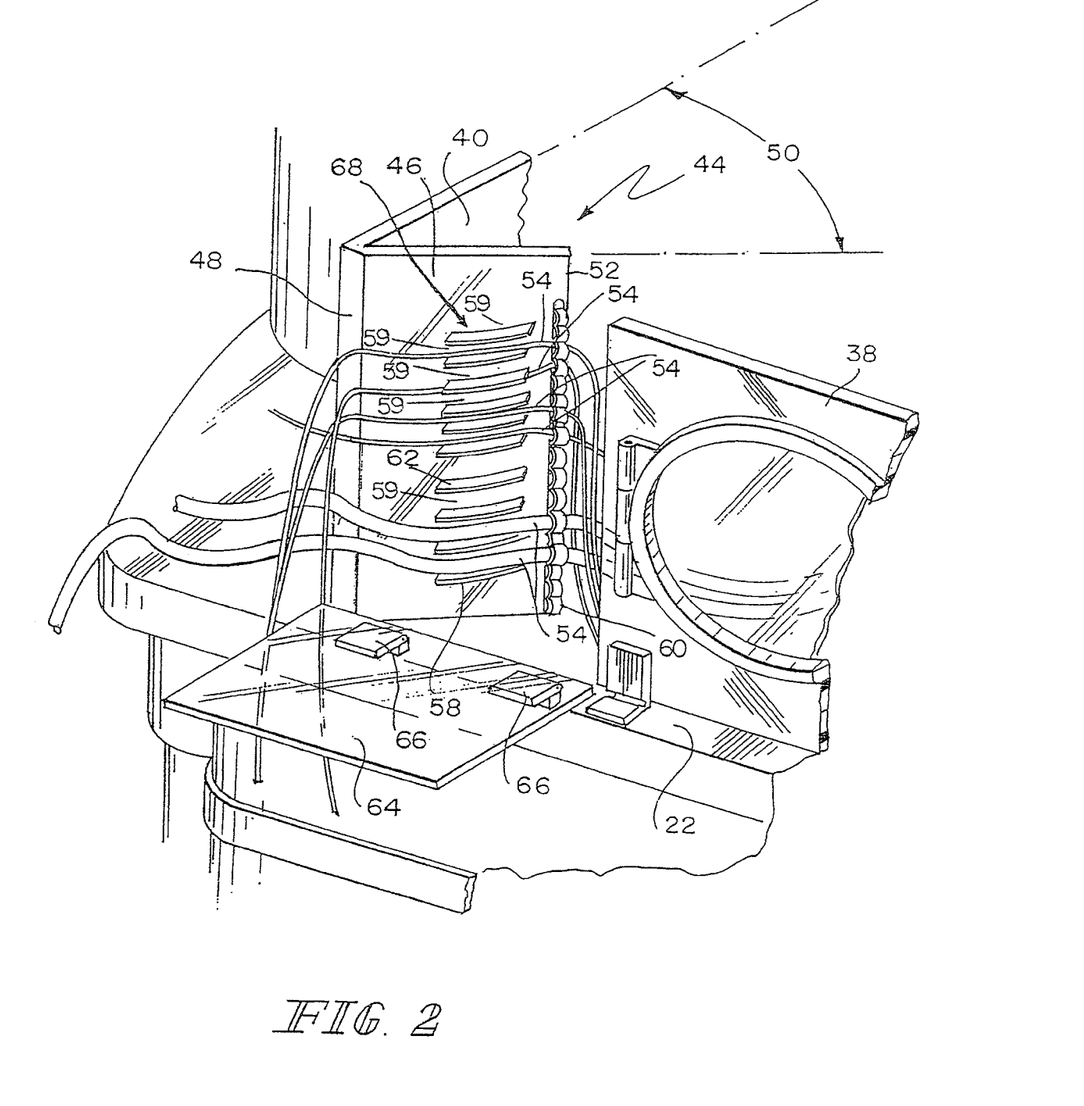
FIG. 2 is an enlarged perspective view of the line port and access door of FIG. 1, showing the line port positioned adjacent one end of a side guard panel, and showing the line port having a vertical panel or wall, a plurality of horizontally extending line supports coupled to the panel, and a plurality of line holders coupled to the panel.

The line port 44 illustrated in FIG. 2 is positioned adjacent one end of side guard panel 38. Port 44 has a line port wall 46 that extends from end guard panel 40. Illustratively, line port wall 46 extends from edge 48 of end guard panel 40 at an angle 50 relative to end guard panel 40. Angle 50 is illustratively an acute angle that positions line port wall 46 such that a vertically extending slot or space is formed between inner edge 52 and side guard panel 38, the slot being wide enough to allow the passage of lines 54 therethrough.

Figure 3:
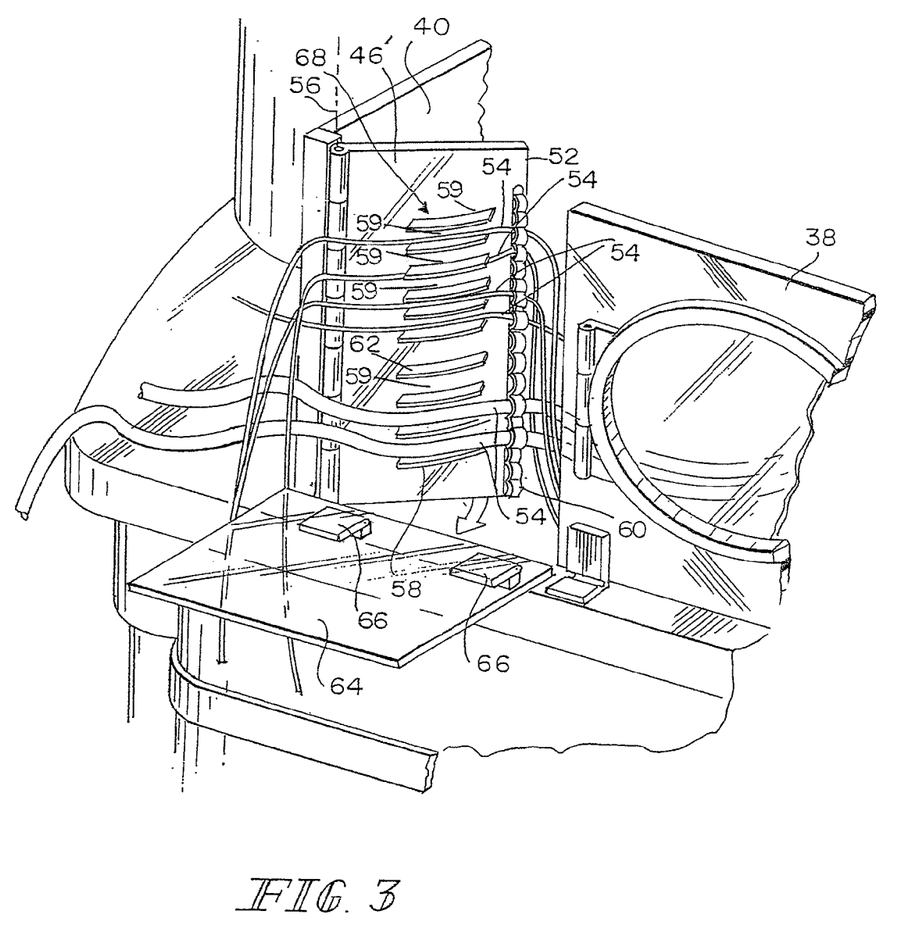
FIG. 3 is an enlarged perspective view of the line port and access door, similar to that of FIG. 2, showing an alternative embodiment having a movable line port wall.

Another embodiment is shown in FIG. 3, wherein line port wall 46' is hingedly connected for movement relative to end guard panel 40. Such a configuration allows line port wall 46' to pivot about a horizontal axis 56 relative to end guard panel 40, thereby moving inner edge 52 either closer to or farther away from side guard panel 38. In operation, a caregiver inserts medical lines 54 into the appropriate places on line port wall 46', and then pivotably moves line port wall 46' closer toward side guard panel 38 so that the slot between inner edge 52 and side guard panel 38 is minimized.

As shown in FIGS. 2-3, line port 44 comprises line port walls 46, 46', a plurality of plates or line supports 58, and a plurality of line holders 60. An air space 59 is located above each line support 58. Line supports 58 have top surfaces 62 that support respective lines 54 in respective air spaces 59 as clearly shown in FIGS. 2 and 3, thereby organizing and arranging the lines 54 that are routed into the isolation chamber of patient-support apparatus 10. Line supports 58 extend substantially orthogonally from line port wall 46, 46'. In some embodiments, supports 58 are formed integrally with line port wall 46, 46' and in other embodiments, supports 58 are separate pieces that couple to wall 46, 46'. Although illustrative supports 58 are plate-like elements, it is within the scope of this disclosure for other structures, such as posts, tabs, hooks, fingers, and the like, as well as grooves, channels, or recesses formed in wall 46, 46', to be used as line supports. As a result, the term "line support" as used in this disclosure, including in the claims, is intended to broadly cover all of these structures and the equivalents thereof.

Illustratively, each line holder 60 is in horizontal alignment and associated with a respective line support 58. Line holders 60 are illustratively C-shaped clamps or pairs of closely spaced fingers made of a resilient material that is pliable so that lines 54 can be inserted therebetween. However, it is within the scope of the disclosure to utilize any method of retaining lines 54 proximate to line port wall 46, 46'. For example, line holders including hook-and-loop straps, hooks, straps with snaps, latches, clasps, clamps, and the like are within the scope of this disclosure. As a result, the term "line holder" as used in this disclosure, including in the claims, is intended to broadly cover all of these structures and the equivalents thereof.

It should be understood that the disclosure also anticipates that line supports 58 and line holders 60 need not be used together, but could be used individually. For example, only one of line holders 60 or line supports 58 could be coupled to line port walls 46, 46', and still provide at least some arrangement to lines 54 leading into the isolation chamber of patient-support apparatus 10.

Illustratively, a door 64 is coupled to platform cover 22 for pivotable movement relative to the platform cover 22. As shown in FIGS. 2-3, door 64 is coupled to platform cover 22 with hinges 66. Door 64 moves about a horizontal axis between an open horizontal position, shown in FIGS. 2-3, and a closed vertical position, shown in FIG. 1. In the closed position, door 64 is in side-by-side relation with side panel 38, and door 64 limits the amount of air that can exchange between the atmosphere and the patient-support apparatus by substantially covering line port 44. In the illustrated embodiment, a gap or passageway (not shown) is formed between edge 48 and door 64 when door 64 is in the closed position. The passageway permits the passage of lines 54 between edge 48 and door 64 without displacement of door 64 into a non-closed position, and without compression of lines 54. When door 64 is in the closed position, top edge 65 of door 64 is configured to confront or be positioned proximate to bottom edge 67 of canopy 34, as shown in FIG. 1.

Each of line supports 58 is illustratively formed such that a first end 68 contacts door 64 when door 64 is in the closed position. Such contact prevents lines 54 from being inadvertently moved to another line support 58 when door 64 is in the closed position.

Figure 4:
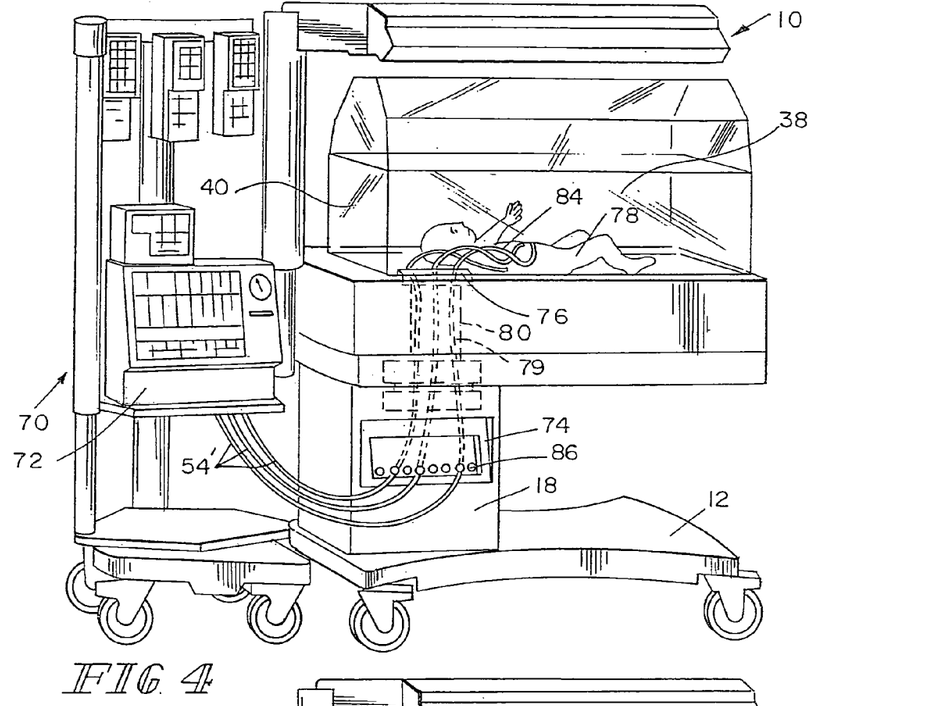
FIG. 4 is a perspective view of a patient-support apparatus and a monitoring station joined therewith, the patient-support apparatus having an electronic terminal mounted on its base and in communication with the monitoring station.

In another embodiment, patient-support apparatus 10 is configured to be coupled with a monitoring cart 70, as shown in FIG. 4. Monitoring cart 70 illustratively includes monitor 72 configured to communicate with patient-support apparatus 10 via at least some of lines 54'. Patient-support apparatus 10 includes a first line port or terminal 74 mounted on pedestal 18, terminal 74 providing connections for lines 54'. Lines 54' illustratively connect to contact 86 on a front surface of terminal 74. Terminal 74 is in communication with platform terminal 76 via internal lines 79 housed within patient-support apparatus 10. It should be understood that the present disclosure contemplates that terminal 74 can be mounted on any portion of patient-support apparatus 10, and not only pedestal 18.

Illustratively, a second line terminal 76 is accessible in the isolation chamber within the parallelogram formed by the side guard panels and end guard panels. The terminal 76 is secured to platform cover 22 near the junction of side guard panel 38 and end guard panel 40, for the purpose of positioning terminal 76 away from contact with patient 78, as shown in FIG. 4. Terminal 76, and likewise terminal 74, may be configured to provide electrical connectors, fluid connectors, or any other type of connector known in the art. Connectors, as defined herein, are associated with a terminal and used to connect a line to the terminal.

Also illustratively, connecting lines 79 that connect terminal 76 to terminal 74 are housed within housings 80, illustrated in phantom in FIG. 4. Patient lines 84 connect to second line terminal 76, and can provide electronic communication or fluid communication with patient 78. For example, patient lines 54, 84 may transmit oxygen, a heart rate signal, temperature signals, a pulse oximetry signal, a respiratory rate, a noise detection signal, or any other fluid or physiologic indicator or electronic signal known in the art. However, it should be understood that lines 54, 84 are not limited to conducting electric signals or fluids, and may provide connectivity for other substances such as, for example, sound pulses. Although the illustrated embodiment shows connecting lines 79 housed internally, it is within the scope of the disclosure to have at least portions of lines 79 disposed outside of pedestal 18 or canopy 34.

Illustratively, patient-support apparatus 10 is configured such that connecting lines 79 are accessible for maintenance, replacement, and sterilization. It is advantageous that a need for line pass-throughs is eliminated by the provision of terminals 74, 76 and internal connecting lines 79. Access ports for accessing the patient may still be provided.

Figure 5:
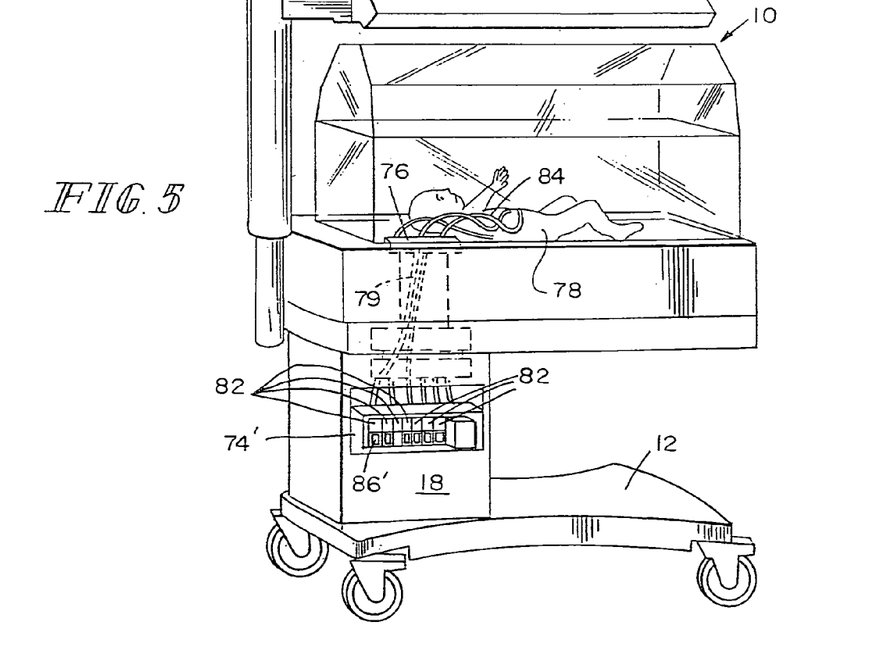
FIG. 5 is an embodiment of the patient-support apparatus similar to that shown in FIG. 4, wherein the terminal includes a plurality of detachable modules.

Yet another embodiment is illustrated in FIG. 5, wherein terminal 74' is either detachable or includes a plurality of detachable modules 82. In such an embodiment, each of detachable modules 82 can be constructed to be specific to a particular use, and thereby provide a port specific to a particular need that is independent of the adjoining port. For example, one detachable module 82 may be configured to electronically report a pulse, while another module 82 may be configured to direct intravenous fluids to the patient 78. In such a construction, modules 82 may be disposable.

Modules 82 are illustratively configured to provide an automatic connection upon insertion into terminal 74'. For example, a module 82 can be configured to include a contact surface with an electric lead that in turn contacts an internal electric lead when mounted on terminal 74'. Other modules 82, for example those conducting fluids, may be configured and mounted in a similar manner. Upon mounting module 82, lines 54' are coupled to contact 86' on the front face of module 82. It is within the scope of the disclosure to also mount an on-board computer (not shown) on the patient-support apparatus. In such a case, lines 54' and/or other lines (not shown) routed through apparatus 10 couple terminal 74' with the on-board computer.

Figure 6:
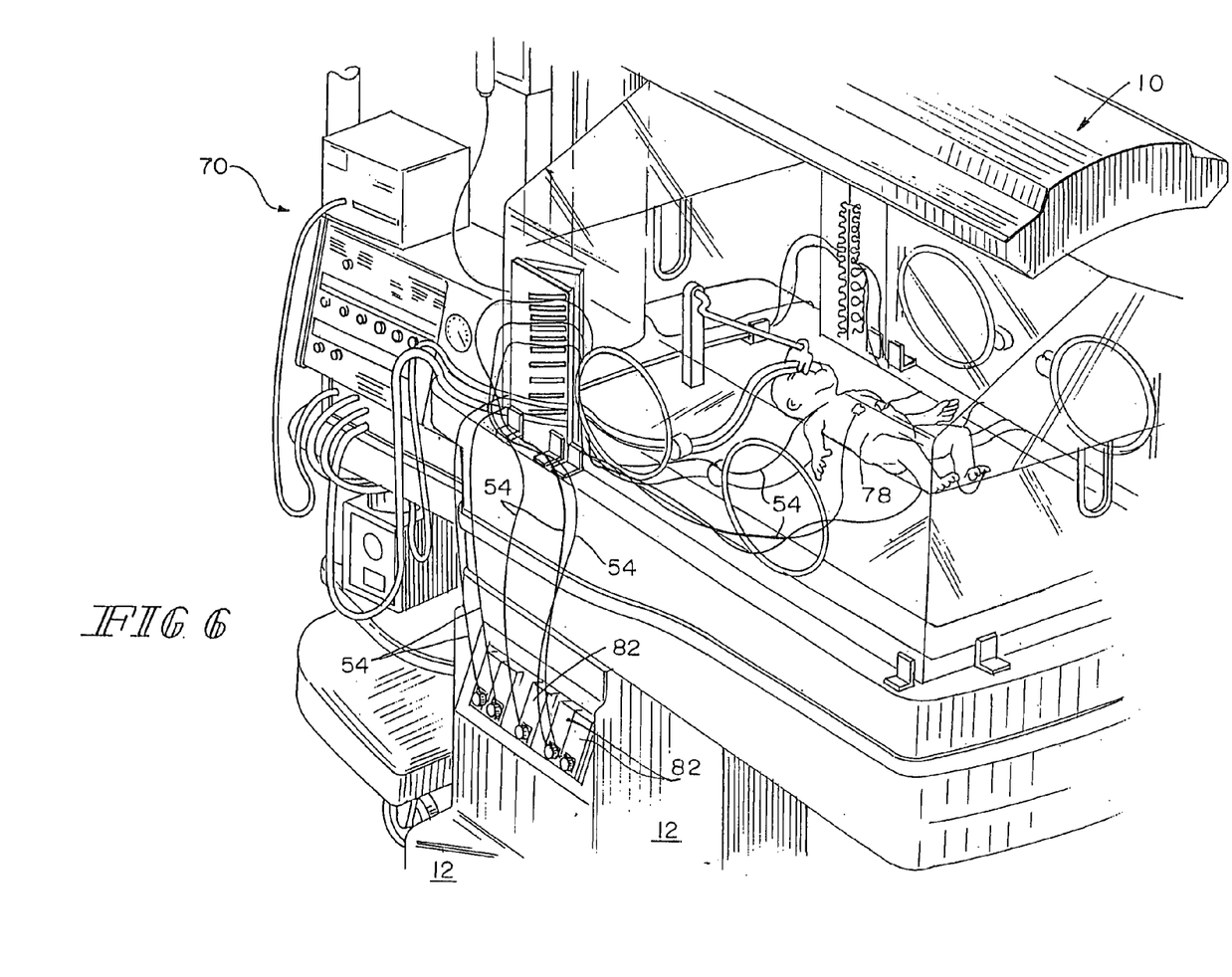
FIG. 6 is another embodiment of the patient-support apparatus similar to that shown in FIGS. 4 and 5, wherein lines extend from the modules through the line port and into the isolation chamber.

Yet another embodiment of the present disclosure is shown in FIG. 6. In such an embodiment, lines 54" are disposed between modules 82 and patient 78. However, lines 54" are disposed outside of pedestal 18 and pass through line port 44 in order to reach patient 78. Cart 70 is illustratively in electronic communication with modules 82 via internal wiring (not shown) routed at least partially through pedestal 18.

While the disclosure is susceptible to various modifications and alternative forms, specific exemplary embodiments thereof have been shown by way of example in the drawings and have herein been described in detail. It should be understood, however, that there is no intent to limit the disclosure to the particular forms disclosed, but on the contrary, the intention is to cover all modifications, equivalents, and alternatives falling within the spirit and scope of the disclosure as defined by the appended claims.

There is a plurality of advantages of the present invention arising from the various features of the line management system and associated method described herein. It will be noted that alternative embodiments of the line management system and associated method may not include all of the features described yet still benefit from at least some of the advantages of such features. Those of ordinary skill in the art may readily devise their own implementations of a line management system and associated method that incorporate one or more of the features of the present invention and fall within the spirit and scope of the present invention as defined by the appended claims.

The invention claimed is:

1. An infant support device comprising
   a support platform,
   an infant enclosure coupled to the support platform and defining an infant compartment for receiving an infant, and
   a line-management apparatus configured to separate and arrange medical lines routed from outside the infant compartment into the infant compartment, the line-management apparatus comprising a panel extending upwardly relative to the support platform, at least a first and a second vertically spaced plates forming a plurality of line supports coupled to the panel and configured to support the medical lines, at least a first and a second air-space, and at least a first and a second line holder, each of the plates being an elongated member extending horizontally in a cantilever manner from the panel and having an upper support surface and a lower surface, the upper surface forming a line support, the first air-space being located above the upper surface of the first plate, the second air space being located between the lower surface of the first plate and the upper surface of the second plate, each of the air-spaces being arranged to receive a longitudinally extending portion of a respective one of the medical lines, whereupon each respective medical line is supported on a respective line support, the plurality of line holders being coupled to the panel and configured to inhibit movement of the medical lines off of the line supports.

2. An infant support device comprising
a support platform,
an infant enclosure coupled to the support platform and defining an infant compartment for receiving an infant, and
a line-management apparatus configured to separate and arrange medical lines routed from outside the infant compartment into the infant compartment, the line-management apparatus including a panel extending upwardly relative to the support platform, a plurality of vertically spaced line supports coupled to the panel and configured to support the medical lines resting thereon, and a plurality of line holders coupled to the panel and configured to inhibit movement of the medical lines off of the line supports, the plurality of line supports comprising a plurality of plates extending from the panel in a cantilevered manner, the infant enclosure comprising a door panel, each plate of the plurality of plates has an edge that faces away from the panel, and the door panel is pivotable about an axis relative to the support platform between a first position covering the edges, and a second position uncovering the edges.

3. The infant support device of claim 2, wherein the axis is a horizontal axis.

4. The infant support device of claim 2, wherein the door panel is oriented substantially vertically when in the first position and the door panel is oriented substantially horizontally when in the second position.

5. The infant support device of claim 2, wherein the infant enclosure comprises a side panel extending upwardly from the support platform and the door panel is aligned in side-by-side relation with the side panel when the door panel is in the first position.

6. The infant support device of claim 2, wherein the infant enclosure comprises an end panel coupled to the support platform, a gap is defined between the door panel and the end panel when the door panel is in the first position, and each of the medical lines supported on the plates extends through the gap.

7. The infant support device of claim 2, wherein the infant enclosure comprises a canopy situated above the infant compartment, the canopy has a bottom edge, and the door panel has a top edge that confronts the bottom edge of the canopy when the door panel is in the first position.

8. An infant support device comprising, a support platform, an infant enclosure coupled to the support platform and defining an infant compartment for receiving an infant, and a line-management apparatus configured to separate and arrange medical lines routed from outside the infant compartment into the infant compartment, the line-management apparatus including a panel extending upwardly relative to the support platform, a plurality of vertically spaced line supports coupled to the panel and configured to support the medical lines resting thereon, and a plurality of line holders coupled to the panel and configured to inhibit movement of the medical lines off of the line supports, the panel is being pivotable relative to the support platform about an axis, the infant enclosure including a guard panel extending upwardly from the support platform and the panel is pivotably coupled to the guard panel.

9. An infant support device comprising:
a support platform having an interior region,
an infant enclosure coupled to the support platform and defining an infant compartment arranged to be opened for receiving an infant,
a first line port or terminal coupled to the support platform and situated outside the infant compartment,
a second line port or terminal coupled to the support platform and situated inside the infant compartment,
a housing defining an enclosed passageway extending therethrough irrespective of whether or not the infant compartment is open or closed, the enclosed passageway being situated between the first line port or terminal and the second line port or terminal, and
at least one internal connection line situated at least partly in the interior region of the support platform, the at least one internal connection line extending through the enclosed passageway in the housing and being coupled to the first line port or terminal and to the second line port or terminal.

10. The infant support device of claim 9, wherein the at least one internal connection line comprises at least one first line electrode.

11. The infant support device of claim 9, wherein the first line port or terminal is detachable.

12. The infant support device of claim 9, wherein the at least one internal connection line conducts a fluid.

13. The infant support device of claim 9, wherein the at least one internal connection line conducts electricity.

14. An infant support device configured to present a line to a patient, the device comprising
a base,
a patient support carried by the base, and
a substantially planar guard panel configured to extend upwardly from the base on at least one side of the patient support,
wherein the guard panel includes a line port having a line holder and a line support, wherein the port has a first surface defining a first plane substantially parallel to the guard panel, and the port has a second surface defining a second plane angled from the first plane and wherein the port cooperates with the guard panel to define a vertically extending slot therebetween, the infant support device further comprising an access door configured to substantially cover the defined slot.

15. The infant support device of claim 14, wherein the access door is pivotably connected to the base.

16. The infant support device of claim 15, wherein the access door contacts the line holder when the access door is in a closed position.

17. An infant support device configured to present a line to a patient, the device comprising
a base,
a patient support carried by the base, and
a substantially planar guard panel configured to extend upwardly from the base on at least one side of the patient support,
wherein the guard panel includes a line port having a line holder and a line support, the line port being pivotably connected to the guard panel.

* * * * *